United States Patent [19]

Kohsai

[11] Patent Number: 5,017,259

[45] Date of Patent: May 21, 1991

[54] PREPARATION OF CATHETER INCLUDING BONDING AND THEN THERMOFORMING

[75] Inventor: Tadashi Kohsai, Fuji, Japan

[73] Assignee: Terumo Kabushiki Kaisha, Tokyo, Japan

[21] Appl. No.: 419,033

[22] Filed: Oct. 10, 1989

[30] Foreign Application Priority Data

Oct. 13, 1988 [JP] Japan .................................. 63-257845

[51] Int. Cl.$^5$ ..................... A61M 25/00; B29C 65/02; B29C 65/48

[52] U.S. Cl. .................. 156/294; 156/304.2; 156/304.6; 156/308.6; 156/309.3; 156/309.6; 264/248; 604/280

[58] Field of Search ..................... 156/158, 294, 303.1, 156/304.2, 304.6, 309.3, 309.6, 308.6; 604/280; 264/248

[56] References Cited

U.S. PATENT DOCUMENTS

| | | |
|---|---|---|
| 3,605,750 | 9/1971 | Sheridan et al. ..................... 604/280 |
| 3,890,976 | 6/1975 | Bazell et al. ........................ 604/280 |
| 4,022,500 | 5/1977 | Van Den Beld ..................... 285/332 |
| 4,044,765 | 8/1977 | Kline ................................. 604/282 |
| 4,263,236 | 4/1981 | Briggs et al. ........................ 264/248 |
| 4,361,152 | 11/1982 | Patel ................................... 604/280 |
| 4,385,635 | 5/1983 | Ruiz ................................... 604/280 |
| 4,419,095 | 12/1983 | Nebergall et al. ..................... 604/96 |
| 4,531,943 | 7/1985 | Van Tassel et al. ................. 604/280 |
| 4,551,292 | 11/1985 | Fletcher et al. ..................... 604/280 |
| 4,563,181 | 1/1986 | Wijayarathna et al. ............. 604/280 |
| 4,636,272 | 1/1987 | Riggs ................................. 156/158 |
| 4,886,506 | 12/1989 | Lovgren et al. ..................... 604/280 |

FOREIGN PATENT DOCUMENTS

| | | |
|---|---|---|
| 0144629A3 | 6/1985 | European Pat. Off. . |
| 0136719 | 7/1979 | Fed. Rep. of Germany ...... 156/158 |
| WO88/06465 | 9/1988 | PCT Int'l Appl. . |
| 1152546 | 5/1969 | United Kingdom . |

OTHER PUBLICATIONS

Webster's New Collegiate Dictionary, 1977, p. 1210.
European Search Report.

Primary Examiner—Michael W. Ball
Assistant Examiner—Steven D. Maki
Attorney, Agent, or Firm—Frishauf, Holtz, Goodman & Woodward

[57] ABSTRACT

A catheter is manufactured by tapering a distal portion of a hollow catheter body, bonding a tip member of relatively soft material to the tapered distal portion of the catheter body, and thermoforming the catheter body distal portion and the tip member.

10 Claims, 5 Drawing Sheets

PREPARATION OF CATHETER INCLUDING BONDING AND THEN THERMOFORMING

BACKGROUND OF THE INVENTION

1. Field of the Invention

This invention relates to a method for preparing a catheter adapted to be inserted into the human body cavity, especially a guiding catheter for use in radiographic examination of the heart and surrounding tissues.

2. Prior Art

In the practice of percutaneous transluminal coronary angioplasty (PTCA), for example, a guiding catheter is first inserted until its distal end is located at the desired site, and a dilating catheter is then inserted into the lumen of the guiding catheter and guided to the site for dilating the stricture.

The guiding catheter for use in such operation typically has a tip portion of soft material such that it does not damage the vessel, heart or surrounding tissues upon insertion of the guiding catheter. Guiding catheters of this type are prepared in the prior art by constructing a catheter body from a resinous material such as flexible vinyl chloride and nylon, and impregnating an end portion of the catheter body with a plasticizer for plasticizing the end portion. This method has several drawbacks including inconsistent flexibility or softness imparted to the catheter end portion, difficulty to freely select the degree of softness, and complexity in the manufacturing process due to the addition of plasticizer impregnating step.

Another catheter manufacturing method is known in the art and described with reference to FIG. 6. There are prepared a catheter body 1 having a lumen 2 and an annular tip member 4 of a softer material than the catheter body 1. A core or skewer mandrel 6 is inserted through the catheter body 1 and the tip member 4. The mandrel 6 is moved into the cavity of a heated mold 8 to urge the tip member 4 and the catheter body 1 against the bottom of the mold cavity. The catheter body 1 is closely mated with the tip member 4 by further pulling the mandrel in a direction shown by arrow A. Then the tip member 4 and the adjacent portion of catheter body 1 are fuse welded at their mating ends and concurrently thermoformed on the outer surface.

This method often results in incomplete fusion welds partly because of the difference in material between the catheter body and the tip member. The tip member located close to the bottom of the mold cavity is first melted and bonded to the adjacent portion of catheter body 1 which has not been fully melted. In addition, the bonding area is small due to the fact that the tip member and the catheter body abut one another at their end surfaces. All these facts contribute to a reduced bond strength. The thermoformed tip members have varying length and poor outer appearance or surface smoothness, contributing to reduced productivity.

SUMMARY OF THE INVENTION

Therefore, an object of the present invention is to provide a method for preparing a catheter by which a tip member is firmly bonded to a catheter body while presenting improved appearance and configuration.

According to one aspect of the present invention, a catheter is manufactured by preparing a catheter body having a distal portion and a lumen axially extending through the body to the distal end, bonding a tip member of a material softer than the catheter body to the distal portion of the catheter body, and thermoforming the catheter body distal portion and the tip member.

Preferably, the distal portion of the catheter body is tapered such that the tip member may be smoothly fitted a sufficient distance over the catheter distal portion, facilitating and augmenting the bonding of the tip member to the catheter distal portion.

According to another aspect of the present invention, a catheter is manufactured by preparing a catheter body having a distal portion and a lumen axially extending through the body to the distal end, tapering the distal portion of the catheter body, engaging a tip member of a material softer than the catheter body over the tapered distal portion of the catheter body, and heating the catheter body distal portion and the tip member thereby thermoforming and bonding them together.

A single step of forming a catheter body having a tapered distal portion may include both the steps of preparing a catheter body and tapering the distal portion of the catheter body.

BRIEF DESCRIPTION OF THE DRAWINGS

The above and other objects, features, and advantages of the present invention will be better understood from the following description taken in conjunction with the accompanying drawings, in which.

Like parts are designated by the same reference numerals throughout the figures.

DESCRIPTION OF THE PREFERRED EMBODIMENTS

Successive steps of the catheter manufacturing method according to the present invention are now described with reference to FIGS. 1 to 5.

(1) Tapering step

Figure 1:
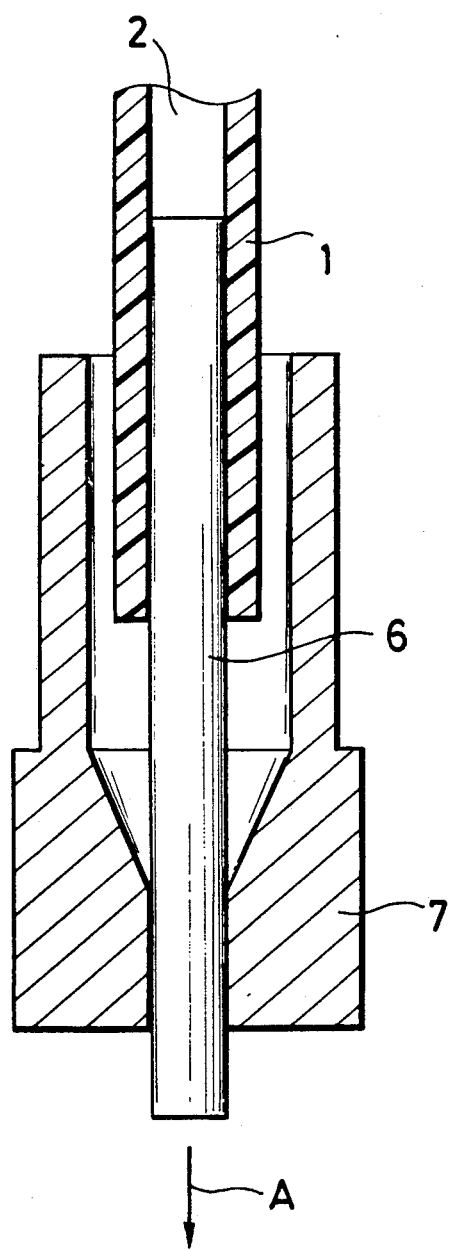
FIGS. 1 to 5 are axial cross sections illustrating successive steps of the catheter manufacturing method according to the present invention.

Referring to FIG. 1, there is first prepared a catheter body 1 having a distal end portion and a lumen 2 axially extending therethrough to the distal end. The catheter body is constructed from a flexible material such as polyvinyl chloride, polyurethane, polyethylene, polypropylene, nylon, and vinyl acetate copolymers. Most often, the flexible material of the catheter body has a hardness of about 96 or higher in Shore A hardness. If desired, the catheter body 1 may be formed with another lumen in addition to the center lumen 2 as well as side ports communicating to the center lumen or other lumen if any, although these components are not shown in the figure. Also, an inflatable balloon may be attached to the catheter body 1 if desired.

Figure 2:
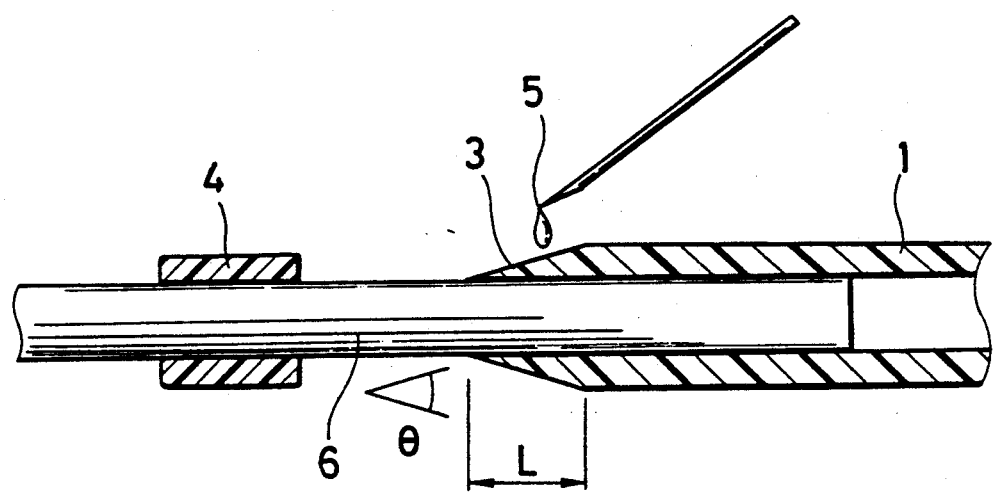

As shown in FIG. 1, a core or skewer mandrel 6 is inserted into the lumen 2 of the catheter body 1 from its opening. The mandrel 6 has an outer diameter substantially equal to or slightly smaller than the inner diameter of the catheter body 1 so that the mandrel is in close contact with the catheter body 1. The mandrel 6 having the catheter body 1 fitted thereon is inserted into a mold 7 which has a convergent cavity and is heated at an appropriate temperature. The mandrel 6 is moved in a direction shown by arrow A to urge the distal portion of the catheter body against the bottom of the mold cavity. Then the distal portion of the catheter body is thermoformed into a tapered portion 3 conforming to the convergent cavity as shown in FIG. 2.

The tapered portion 3 of the catheter body 1 has an axial length L which varies with the type and use of a particular catheter. For example, the axial length L of the tapered portion is about 2 mm to about 10 mm for PTCA guiding catheters. The tapered portion 3 preferably has a taper angle $\theta$ (see FIG. 2) of from about 5° to about 45°, more preferably from about 5° to about 30°. The distal portion of the catheter body is tapered for the purposes of increasing a bonding area or an area anticipated to be heated upon thermoforming and smoothing the transition between the different members. With a taper angle of smaller than 5°, it will be difficult to achieve a smooth continuous transition (at 31 in FIG. 5) between the softer tip member and the catheter body. The tip member is likely to strip away without a smooth transition. A taper angle of larger than 45° is rather inadequate for the purpose of increased bonding area and hence increased bond strength. A similar tendency would be found with a too long or too short length L of the tapered portion 3.

The tapered portion 3 is preferably of a frustoconical shape having a taper angle $\theta$ as defined above although the invention is not limited thereto. The distal portion of the catheter body may have any forward convergent shape whose transverse cross-sectional area decreases toward the distal end, for example, a convergent shape having a radially outwardly convex or concave side surface. Also contemplated is a forward convergent shape whose transverse cross-sectional area decreases stepwise toward the distal end. Broadly stated, the distal portion of the catheter body is an outer diameter reducing portion having a outer diameter reducing toward its extreme end, that is, a smaller outer diameter at its extreme end than at its base. It is to be noted that the inner or lumen diameter is substantially fixed. For such a distal portion whose outer diameter decreases non-linearly toward the extreme end, a phantom taper surface defined by connecting the extreme end and the base may meet a taper angle range as defined above.

The tapering mold 7 may typically be heated to a temperature of about 150° to about 250° C. by RF induction heating or resistance heating.

The tapering of the distal portion of the catheter body is not limited to the thermoforming process illustrated above and the catheter body distal portion may be tapered by machining or solvent removal, for example. Of course, the tapered portion 3 of the catheter body 1 may be provided at the same time as the catheter body 1 is formed. As compared with concurrent formation, separate tapering is somewhat advantageous from the standpoints of precision and consistency.

The tapered portion 3 provides an increased joint or bond area between the catheter body 1 and the tip member 4, resulting in an increased bond strength. An increased area to be heated upon thermoforming ensures such an increase of bond strength. Other advantages are dimensional stability, smooth and anti-strip transition.

(2) Bonding step

A fluid adhesive 5 is applied to the tapered portion 3 of the catheter body 1 on the mandrel 6 as shown in FIG. 2. An annular tip member or soft tip 4 which has been separately prepared is fitted over the mandrel 6 in spaced relation to the tapered portion 3 preferably before the adhesive application.

Figure 3:
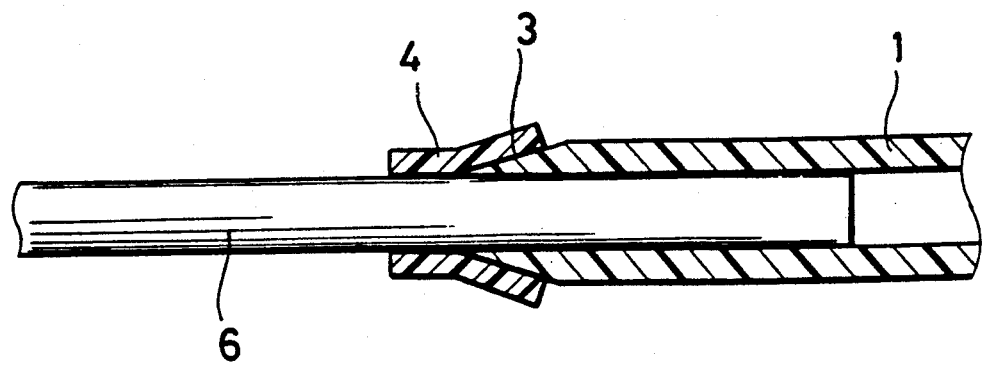

Then the tip member 4 is axially moved along the mandrel 6 until it covers the tapered portion 3 as shown in FIG. 3. Then the tip member 4 is bonded to the tapered portion 3.

The tip member 4 has an inner diameter substantially equal to that of the catheter body 1 and an axial length which varies with the type and use of a particular catheter. For example, the axial length of the tip member is about 2 mm to about 10 mm for PTCA guiding catheters. Preferably, the tip member 4 overlaps the tapered portion 3 a distance of about 50% to about 90% of the tip member length. That is, the majority of the tip member 4 is bonded to the tapered portion 3.

The tip member 4 is constructed of a softer material than the catheter body, for example, flexible polyvinyl chloride (PVC), polyurethane, and polyamide, with the polyurethane and PVC being preferred. The tip member preferably has a hardness of up to about 95, more preferably from about 70 to about 95, most preferably from about 80 to about 90 in Shore A hardness scale. A hardness of more than 95 in Shore A is less desirable because such harder tip members would often cause damage to the patient body cavity upon catheter insertion. In turn, a tip member with a hardness of less than 70 in Shore A is permissible because the tip member of a reduced length can prevent blockage of its lumen due to collapse.

The hardness of the tip member 4 may be controlled by changing the amount of a plasticizer blended in a molding composition for the tip member. The plasticizer may be selected for a particular resin, although typical examples are di(2-ethylhexyl) phthalate (DOP) and para-hydroxybenzoic acid ethyl hexyl (POBO). Of course, the tip member 4 of a desired hardness may be formed of a selected type of resin without resorting to the plasticizer.

Since the catheter is used as indwelled in the patient body, there is a need that the position of the catheter distal end be visually observed by radiography while the catheter is manipulated for insertion. To this end, the catheter is preferably made radiopaque. More particularly, a radiopaque agent is preferably blended in the material of which the catheter body and/or tip member is formed. Examples of the radiopaque or contrast agent include barium sulfate, bismuth oxide, tungsten, lead, iron, and silver.

Adhesive bonding of the tip member 5 has been illustrated in the foregoing embodiment although solvent welding techniques and fusion bonding techniques such as heat welding and ultrasonic fusion welding may also be employed in the practice of the invention. The bonding used herein thus encompasses all these types of bond.

The adhesive used in bonding the tip member 4 to the distal portion of the catheter body may be selected from polyurethane and acrylic adhesives, for example. For solvent welding, tetrahydrofuran (THF), cyclohexanone and other commonly used solvents may be employed. Preferred are adhesives and solvents in which solvent component will readily volatilize upon heating. A choice of such a volatile adhesive or solvent has an advantage of increased safety to the patient because the solvent component of the adhesive or the solvent itself will readily evaporate off upon subsequent thermoforming of the distal portion of the catheter body. Examples of such volatile solvent are THF and cyclohexanone and typical volatile adhesives are urethane adhesives based on THF solvent.

Bonding the tip member to the catheter body tapered portion prior to thermoforming step (3) has an advantage of increased alignment between the tip member and the tapered portion. Registry bonding followed by thermoforming provides several advantages including increased bond strength, dimensional stability, and smooth and anti-strip transition.

Because of the registry positioning nature of bonding, it is possible to omit tapering step (1) from the method of the invention. Without tapering, problems will arise with concurrent thermoforming and bonding according to the prior art, but a sequence of first bonding and subsequent thermoforming can eliminate such problems.

(3) Thermoforming step

Figure 4:
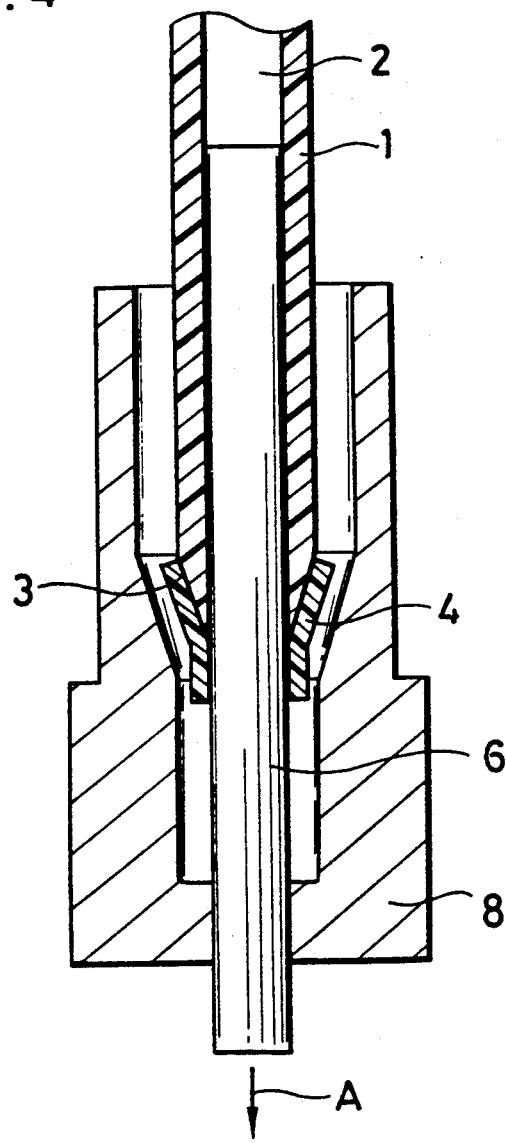
Figure 5:
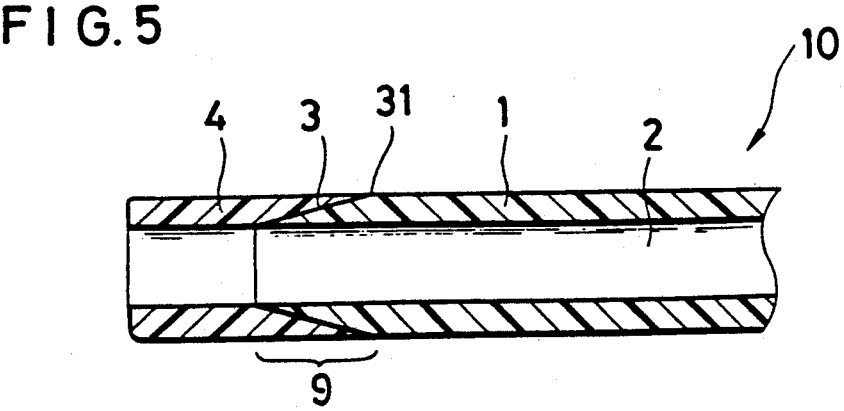

The catheter body 1 having the tip member 4 bonded to its distal portion 3 along with the mandrel 6 carrying them is then inserted into a mold 8 as shown in FIG. 4. The mold 8 has a cavity including a convergent section and a cylindrical section contiguous thereto. The mandrel 6 is moved in a direction shown by arrow A to urge the tip member against the cavity wall while the mold 8 is heated to a predetermined temperature. The tip member and the catheter body distal portion are softened such that they may pass the transition between the convergent and cylindrical cavity sections. In the cylindrical cavity section, the tip member and the catheter body distal portion are sufficiently heated for melt joining therebetween and thermoforming to the configuration of the cylindrical cavity section. This sequence of softening and melting is only for the purpose of description because actual such changes are difficult to describe. There is obtained a catheter 10 having a configuration as shown in FIG. 5. That is, the tip member 4 and the catheter body 1 are bonded over the relatively increased area given by the inclined interface between the tip member and the tapered distal portion such that the outer and inner wall surfaces of the tip member 4 smoothly connect to those of the catheter body 1 as shown in a region 9.

The thermoforming mold 8 may typically be heated to a temperature of about 150° to about 250° C. by RF induction heating, ultrasonic heating or resistance heating. The heating time for thermoforming is generally from about 3 to about 10 seconds.

The process of thermoforming or tip member processing has an advantage that since the tip member 4 is previously bonded to the tapered portion 3 of the catheter body 1, uniform and consistent thermoforming is accomplished, resulting in a catheter which has the tip member 4 attached at high bond strength and having improved nature and appearance or configuration, with an additional advantage of increased productivity.

The catheter of the invention generally has an outer diameter of 1.5 to 3.0 mm, a lumen diameter of 1.0 to 2.2 mm, and a tip length of 1.0 to 10.0 mm between the leading and trailing ends of the thermoformed tip member. Great benefits are obtained when the principle of the invention is applied to thin tubular members of such reduced dimensions.

In the practice of the invention, tapering step (1) may be omitted, that is, the tip member 4 may be attached to the distal portion of the catheter body 1 without tapering and then subjected to thermoforming. In this case, the attachment of the tip member 4 to the catheter body distal portion may be done by abutting the aft end of the tip member 4 to the forward end of the catheter body distal portion or by causing the tip member 4 to overlap the catheter body distal portion. Bonding may be accomplished with the aid of adhesive or heat.

It is, however, preferred to taper the distal portion of the catheter body 1 for several reasons. First, attachment of the tip member 4 to the tapered distal portion 3 of the catheter body can advantageously improve the bond strength because an increased bonding area is available in the transition region 9 in FIG. 5. A second advantage is ease of operation in that the tip member and the catheter body distal portion can be smoothly inserted and compressed in the mold 8 upon thermoforming.

Thirdly, the catheter body 1 of relatively hard material is connected to the tip member 4 of relatively soft material in the transition or bonding region 9 as shown in in FIG. 5. In this tapered connection, the proportion of relatively soft material gradually increases toward the leading end (or the left end in the figure) of the catheter, that is, flexibility continuously increases toward the leading end. As a consequence, when a leading portion of the catheter is bent or twisted upon actual operation, the bending stresses are distributed over the entire bonding region 9 rather than concentrating at a certain point, ensuring that the catheter is bent along a moderate continuous curve, preventing blockage of the lumen 2 and separation or cracking at the bonding region 9 which would otherwise occur due to bending or twisting of the catheter at an acute angle.

Where the distal portion of the catheter body is tapered, it is possible to mount the tip member on the tapered portion, and then heat and compress the overlap to concurrently achieve bonding and thermoforming. In this embodiment, the mold 8 is heated by any desired means to accomplish fusion bonding and thermoforming at the same time.

It is also contemplated to apply a retarded adhesive such as a thermosetting adhesive to the tip member and/or the tapered portion, mount the tip member on the tapered portion, and then heat and compress the overlap, thereby concurrently thermoforming the assembly and thermosetting the adhesive.

A successive process involving bonding followed by thermoforming is rather advantageous over a single heating step capable of concurrent bonding and thermoforming from the standpoint of accurate alignment of the tip member to the tapered portion, resulting in increased dimensional stability, appearance and bond strength.

The catheters manufactured by the present invention include various types of catheters requiring flexibility at the leading or distal end, for example, guiding catheters as previously illustrated, angiographic catheters, and intravenous hyperalimentation (IVH) catheters.

EXAMPLE

Examples of the invention are given below by way of illustration and not by way of limitation.

EXAMPLE 1

A catheter having the structure shown in FIG. 5 was manufactured by following tapering (1), bonding (2), and thermoforming (3) steps as previously described. The specifications are given below.
Catheter use: PTCA guiding catheter Catheter body:
  Outer diameter: 8Fr (diameter 2.67 mm)
  Inner diameter: 1.9 mm (lumen diameter)
  Material: polyurethane
  Hardness: 98 in Shore A hardness
Tapered portion:
  Process: thermoforming by RF induction heating
  Axial length L: 4 mm
  Taper angle: 10°
Tip member:
  Configuration: hollow cylinder
  Axial length: 5 mm
  Material: polyurethane
  Hardness: 80 in Shore A hardness
Bonding solvent: THF
Thermoforming:
  Process: thermoforming by RF induction heating
  Temperature: about 200° C.
  Time: 4 sec.

EXAMPLE 2

A catheter was manufactured by the same procedure as in Example 1 except that the tip member was bonded with a polyurethane adhesive (Saivinol ® UF60, Sanden Kagaku K.K.) instead of the solvent.

EXAMPLE 3

Figure 6:
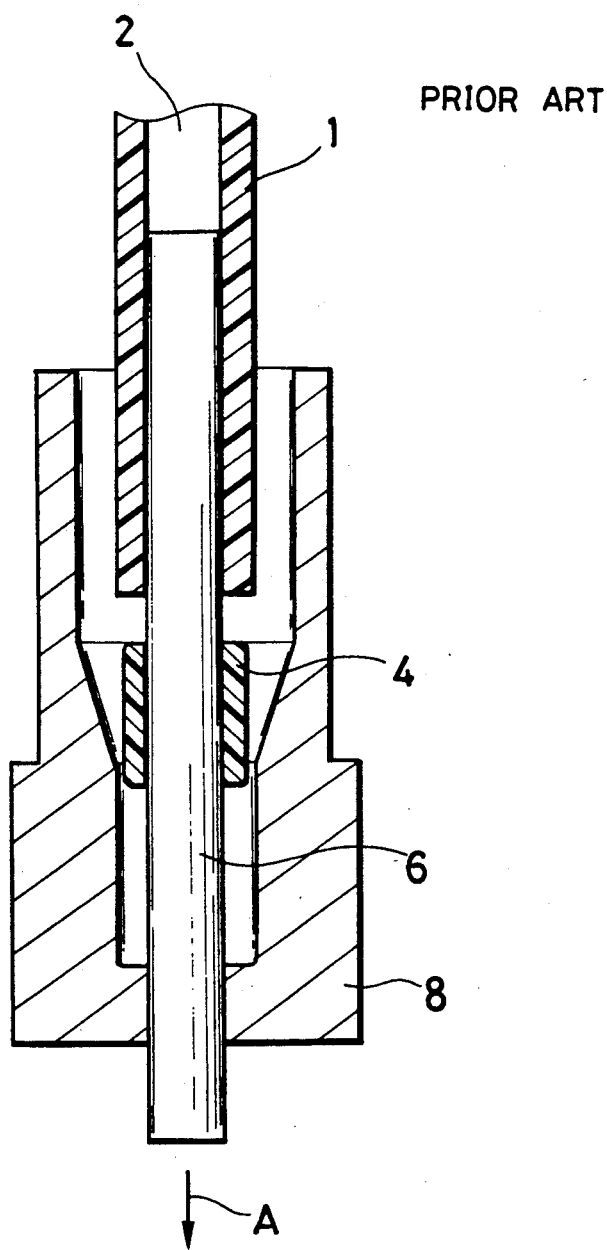
FIG. 6 is an axial cross section showing a prior art catheter manufacturing method.

This is a comparative example outside the scope of the invention. A catheter was manufactured as shown in FIG. 6 using the same components as in Example 1 except that the distal portion of the catheter body was not tapered and the tip member was not previously bonded to the catheter body.

Figure 7:
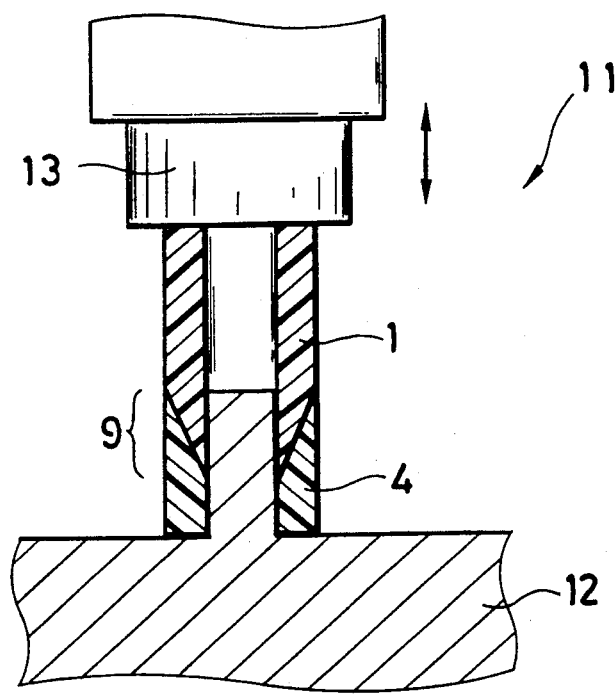
FIG. 7 is an elevational view partially in cross section of a testing arrangement for examining the bond strength of a catheter body-tip member joint.

The catheters of Examples 1-3 were examined for the bond strength between the catheter body and the tip member using a testing arrangement 11 as shown in FIG. 7. A leading section of each catheter was set mounted on a post standing on a base 12 such that the tip member 4 was located underside. Impact loads were applied 100 times to the rear end of the catheter section using a hammer 13 adapted to vertically move up and down over a stroke of 3 mm. The catheter section was removed from the post and examined at the bonding region 9 between the catheter body 1 and the tip member 4.

No defects were found in the bonding region 9 of the catheters of Examples 1 and 2 whereas the tip member separated from the catheter body in the catheter of Example 3.

The catheters of Examples 1-3 were also examined by a repetitive bending test. A leading portion of each catheter was repeatedly bent and straightened 100 times.

In the catheters of Examples 1 and 2, no defects were found in the bonding region 9 and the leading portion did not remain bent. The tip member separated from the catheter body in the catheter of Example 3.

There has been described a catheter manufacturing method in which a tip member is bonded to a distal portion of a catheter body before the catheter leading portion is thermoformed. There is obtained a catheter in which the connection between the tip member and the catheter body has a high bond strength. Uniform and consistent thermoforming results in a catheter having improved nature and appearance or configuration at the leading portion, and increases productivity.

In the preferred embodiment wherein the distal portion of the catheter body is tapered and the tip member is bonded to the tapered distal portion, an increased bond strength is achieved because of the increased bonding area. The leading portion of the catheter in which flexibility continuously increases toward the leading end is resistant against bending and twisting upon actual operation, preventing blockage of the lumen and separation or cracking at the bonding interface which would otherwise occur due to angular bending or twisting of the catheter.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

I claim:

1. A method for preparing a catheter, comprising the steps of
    preparing a catheter body having a distal portion with a distal end, and a lumen axially extending through the body to the distal end,
    processing the distal portion of the catheter body such that the outer diameter of the distal portion reduces toward the distal end,
    bonding a hollow cylindrical tip member of a material softer than the catheter body and having an inner diameter substantially equal to that of the catheter body to the diameter-reducing distal portion of the catheter body, and
    next thermoforming the catheter body distal portion and the tip member such that outer and inner wall surfaces of the tip member connect smoothly to those of the catheter body.

2. The method of claim 1 wherein the steps of preparing a catheter body and processing the distal portion of the catheter body are included in a single step of forming a catheter body having a tapered distal portion.

3. The method of claim 1 wherein the step of processing the distal portion includes forming a tapered portion having a taper angle of about 5 to about 45 degrees.

4. The method of claim 1 wherein the step of processing the distal portion includes thermoforming of the distal portion.

5. The method of claim 1 wherein the step of bonding the tip member to the distal portion includes applying an adhesive or solvent.

6. The method of claim 1 wherein in the step of bonding the tip member over the diameter reducing distal portion of the catheter body, the tip member overlaps the diameter reducing distal portion over a distance of about 50 to about 90% of the axial length of the tip member.

7. The method of claim 3 wherein the step of processing the distal portion includes thermoforming to form the tapered portion.

8. The method of claim 3 wherein the tip member has a hardness of up to 95 in Shore A hardness.

9. The method of claim 3 wherein the material of which the tip member is formed contains a radiopaque agent.

10. The method of claim 1, wherein said next thermoforming step includes forcibly inserting the catheter body while carried on a mandrel and having the tip member bonded to the distal portion of the catheter body, into a mold cavity, and heating the catheter body and the tip member inside the mold cavity.

* * * * *